United States Patent [19]

Ellis et al.

[11] 4,447,528
[45] May 8, 1984

[54] DETECTING INTRINSIC FACTOR BLOCKING SITE ANTIBODY

[75] Inventors: James E. Ellis, Stoughton; Graham P. Lidgard, Wellesley; Gerald Odstrchel, Walpole; Louis J. Riceberg, Needham, all of Mass.

[73] Assignee: Corning Glass Works, Corning, N.Y.

[21] Appl. No.: 291,354

[22] Filed: Aug. 10, 1981

[51] Int. Cl.$^3$ .................. G01N 33/58; G01N 33/82; G01N 33/50

[52] U.S. Cl. .................................... 435/7; 424/96; 424/201; 435/4; 435/177; 436/501; 436/527; 436/804

[58] Field of Search ............... 435/4, 7, 177, 188, 435/805, 810; 424/1, 1.5, 8, 12; 23/230 B; 436/506, 507, 508, 509, 501, 527, 804

[56] References Cited

U.S. PATENT DOCUMENTS

| | | | |
|---|---|---|---|
| 3,615,222 | 10/1971 | Mead ................................. | 23/230 B |
| 3,721,528 | 3/1973 | Mead et al. ....................... | 23/230 B |
| 4,069,352 | 1/1978 | Parsons ............................. | 23/230 B |
| 4,279,859 | 7/1981 | Gutcho et al. ........................... | 424/1 |
| 4,279,886 | 7/1981 | Allen ....................................... | 424/1 |
| 4,292,296 | 9/1981 | Parsons ................................... | 424/1 |
| 4,292,403 | 9/1981 | Duermeyer ............................. | 435/7 |
| 4,347,311 | 8/1982 | Schmitz .................................. | 435/7 |

OTHER PUBLICATIONS

A. K. Sobotka et al., J. Immunol., 117 (1), 84–90 (1976).
D. R. Hoffman, "Methods in Enzymology", vol. 73, 656–666, Academic Press, 1981.
"Clinical Immunology", S. O. Friedman et al., Eds., 2nd Edition, pp. 346–351, Harper & Row, Hagerstown, 1976.
"Immunology", J. Bach, Ed., pp. 624–626, John Wiley & Sons, New York, 1978.
"Clinical Diagnosis and Management", J. B. Henry, 16th Edition, vol. II, 1331–1332, 1420–1429, Todd, Sanford, Davidson, W. B. Saunders, Philadelphia, 1979.
Chemical Abstracts, 66:113903c (1967).
Mathan et al., "Kinetics of the Attachment of Intrinsic Factor-Bound Cobamides to Ileal Receptors", Chem. Absts., vol. 81, No. 25, p. 157 (1974) Abst. No. 164896.
Wolff et al., "Detection and Semiquantitative Biological Determination of the Antigenic Determinants of Human Gastric Intrinsic Factor and of the Antiintrinsic Factor Autoantibodies Present in some Pathological Sera", Chem. Absts. vol. 79, No. 13, 333, (1973), Absts. No. V76788m.
Anderson, "Araprd Polyethylene Glycol Assay for Gastric Intrinsic Factor", Chem. Absts., vol. 92, No. 5, pp. 373–374, (1980), Absts. No. 37155e.
Seetharam, et al., "Isolaton and Characterization of the Ideal Receptor for Intrinsic Factor-Cobalamin J. Biol. Chem., vol. 256, No. 8 (1981) pp. 3785–3790.
Kouvonen et al., "A Simplified Technique to Isolate the Parcine and Human Ileal Intrinsic Factor Receptors and Studies on their Subunit Structors", Biochem. Biophys. Res. Comm., vol. 86, No. 2, (1979), pp. 358–364.
Marcoulis et al., "Identification and Characterization of Intrinsic Factor and Cobalophilin from Prg Ileal and Pyloric Mucosa"B.B.A., vol. 497, (1977), p. 663–672.

Primary Examiner—Sidney Marantz
Attorney, Agent, or Firm—W. E. Maycock

[57] ABSTRACT

A radioassay procedure and reagent kit therefor for detecting auto blocking antibody, such as auto blocking antibody which interferes with the complexation of intrinsic factor with vitamin $B_{12}$. A receptor, i.e., intrinsic factor, is immobilized on a support and the amount of ligand, i.e., vitamin $B_{12}$, capable of binding therewith in the presence of a biological fluid sample is determined.

7 Claims, No Drawings

DETECTING INTRINSIC FACTOR BLOCKING SITE ANTIBODY

BACKGROUND OF THE INVENTION

During many normal biological interactions, various substances in a living organism must bind to one another through their receptor sites. At times, an individual's immune system can create an auto-immunity to one of these substances (often a binder or receptor protein) by production of blocking antibodies (so-called "auto blocking antibody"). The blocking antibodies are competitively attracted to the complementary binding sites on the receptor. Obviously, this reduces the quantity of binding sites available for binding with the complementary substance with which the receptor should normally interact (so-called "ligand"), also often a protein.

One well-known example of a potential auto blocking antibody system is the inter-relationship between intrinsic factor and cobalamine (vitamin $B_{12}$). Intrinsic factor is a glycoprotein responsible for vitamin $B_{12}$ absorption through the gastrointestinal tract. After ingestion, vitamin $B_{12}$ binds to intrinsic factor through specific receptor sites and the complex is absorbed through the mediation of receptors for the complex in the gastrointestinal tract.

In the disease pernicious anemia, there is a gradual decline and eventual absence of the ability to make and secrete intrinsic factor. There is a very high association between pernicious anemia and the presence of auto-immune antibodies, particularly the intrinsic factor blocking antibody.

In situations of the type discussed above, it would be highly useful to be able to at least qualitatively determine the presence of the blocking antibodies, such as those produced for intrinsic factor (hereinafter "IF blocking site antibodies—at this time it is believed that intrinsic factor contains at least two types of binding sites, but only one of which is involved in forming the complex with vitamin $B_{12}$).

Turning to the specific intrinsic factor-vitamin $B_{12}$ situation, the inventors are aware of radioassay procedures used and suggested in the prior art for detecting the presence of IF blocking site antibodies. All of these prior art procedures are believed to involve solution techniques, that is, all reactive reagents are in solution or at least freely suspended within a liquid medium. Quite naturally, the approaches used are selected to take advantage of the ability of the IF blocking site antibodies to inhibit the binding of labeled (i.e., radioactive) vitamin $B_{12}$ to intrinsic factor. In general, intrinsic factor (or gastric juice containing intrinsic factor) is admixed with the patient's biological fluid sample (ex serum) and then the labeled vitamin $B_{12}$ (in excess) is added thereto. It is then necessary to separate bound labeled vitamin $B_{12}$ from free labeled vitamin $B_{12}$. Dialysis, gel filtration, charcoal absorption, and zirconyl phosphate gel absorption have been described as separatory techniques. Apart from these cumbersome and often time-consuming separatory procedures, the prior art solution-based radioassays present difficulties due to the presence of endogenous vitamin $B_{12}$ binder in many patient samples. It is necessary to run an additional control to account for endogeneous vitamin $B_{12}$ binder or to procedurally remove the endogenous binder from the sample.

SUMMARY OF THE INVENTION

The present invention in a specific embodiment overcomes the problems attendant the prior art solution techniques for determining the presence of IF blocking site antibody, and in addition provides a generic procedure useful for detecting other auto blocking antibodies.

Accordingly, it is an object of this invention to provide a process for qualitatively or quantitatively detecting the presence of an auto blocking antibody.

Another object of this invention is to provide a process for detecting the presence of IF blocking site antibodies.

Still another object of this invention is to provide a process for detecting IF blocking site antibodies which is not characterized by the problems involved in employment of the solution systems of the prior art.

A further object of this invention is to provide a diagnostic reagent kit to be used for quantitatively or qualitatively detecting the presence of an auto blocking antibody in a patient.

Another object of this invention is to provide a diagnostic reagent kit to be used for detecting the presence of IF blocking site antibody in a patient.

A more specific object of this invention is to provide a diagnostic reagent kit, including suitable calibrators, for determining the presence of IF blocking site antibody in a patient.

Other objects of this invention will be apparent from the Detailed Description of the Invention hereinbelow.

In accordance with the present invention, an auto blocking antibody is detected by utilizing a unique immobilized receptor in a radioassay procedure.

More specifically, the present invention provides a process for detecting the presence of an auto blocking antibody which comprises:

(a) admixing a biological fluid sample suspected of containing the auto blocking antibody with receptor having selective binding sites for said antibody, said receptor being immobilized on an inanimate support;

(b) incubating the mixture from step (a) under conditions sufficient to enable substantially all of the blocking antibody present to bind to the receptor, whereby a solid phase comprising said inanimate support with the blocking antibody bound thereto and a liquid phase comprising said biological fluid sample without said blocking antibody result;

(c) separating the solid phase from the liquid phase;

(d) admixing a liquid comprising a labeled ligand for said selective binding sites with the separated solid phase;

(e) incubating the mixture from step (d) under conditions sufficient to enable the labeled ligand to bind to the selective binding sites of said receptor which did not bind to said blocking antibody, whereby a second solid phase comprising said inanimate support with at least one of blocking antibody and labeled ligand bound thereto and a second liquid phase comprising unbound labeled ligand result;

(f) separating the second solid phase from the second liquid phase; and (g) determining the amount of labeled ligand present in at least one of the second solid phase and the second liquid phase.

In a preferred embodiment of the present invention, the receptor is a protein.

In another preferred embodiment of the present invention, the receptor is intrinsic factor and the labeled ligand is labeled vitamin $B_{12}$.

In still another preferred embodiment of the present invention, a negative calibration reference and a minimal positive response calibration reference are used during the testing procedure.

Other preferred embodiments of the present invention involve the use of glass beads as the inanimate support with the receptor being covalently bound thereto.

DETAILED DESCRIPTION OF THE INVENTION

As discussed above, the present invention is useful in determining the presence of auto blocking antibody in a qualitative or quantitative fashion. Although the invention will be exemplified by an assay to detect IF blocking site antibody, it is believed that this invention would be equally useful in an analysis for other auto blocking site antibodies, such as in Grave's Disease (determining the presence of auto blocking antibody for thyroid stimulating hormone), Addison's Disease, and so on as long as the receptor can be physically and/or chemically attached to an inanimate support and the labeled ligand can be incubated therewith. The present invention not only provides a process for carrying out the above-described type of assay, but also provides reagent kits for that purpose, including in preferred embodiments two calibrators and where desired a positive control.

The concept of this invention is based on the use of immobilized receptor, most often an immobilized receptor protein. The receptor is the substance having binding sites to which any auto blocking antibody present in the patient's biological fluid sample would be attracted and also may be the substance which normally would bind to the ligand in an in vivo biological interaction. The auto blocking antibody, which is produced by the patient, interferes with the in vivo complex formation between the ligand and the receptor by binding to the receptor at at least some of the binding sites which normally would be available for use in receptor-ligand binding.

The art of attaching protein or other receptor substances to inanimate supports has advanced to the point where it need not be discussed in great detail herein. Although various types of inanimate particles or beads or surfaces can be employed, such as synthetic, i.e., organic polymers, ceramics, inorganic powders, natural polymers, celluloses, agaroses, and the like, the preferred substrate is glass, for example the type of glass particles used in many of the IMMOPHASE ® assay test systems available commercially from Corning Medical and Scientific of Medfield, Mass. These glass beads are most often aminosilane treated and can be of a controlled porosity. The receptor will usually be bound to the substrate through a covalent bond, with or without the use of a spacer moiety, as is well known in the art, depending upon reactant groups present. For example, intrinsic factor can be reacted with controlled pore glass particles via aminosilane coupling and glutaraldehyde as is well known in the art (see, e.g., U.S. Pat. No. 3,669,841). Where suitable, ionic bonding, hydrophobic interactions, van der Waals forces, and the like can also be used, e.g., as in simple adsorption, in immobilizing the receptor on the inanimate support.

The receptor should essentially be the same as that found in the living organism, or selected to mimick the naturally occurring receptor. At times, modifications will occur during extraction, stabilization, and so on, and are acceptable as long as the binding sites of the receptor needed for the analysis are not altered. Of course, most often the receptor will be the analogous material obtained from a lower animal instead of from a human source. Furthermore, it should be possible to utilize another naturally-occurring or even synthetically produced substance as the receptor as long as the binding sites thereof selectively duplicate those of the naturally-occurring receptor. Therefore, the receptor could be nonproteinaceous, such as an ion exchange resin, a hydrophobic material, or the like to which the suspected auto blocking antibody can bind. At times, although the receptor is a protein, the binding occurs through a nonproteinaceous portion of the protein, such as included carbohydrate, lipid and/or peptide moieties. Furthermore, in vitro experiments have shown that some glass particles are capable of mimicking protein receptor surfaces.

The second essential reagent of the present invention is the labeled ligand. Similar to the situation with the receptor, the ligand is preferably the ligand as will be present in the living organism, but could be modified or even be a synthetic material which might not function for its intended purpose in the living organism, as long as the binding sites thereof are those required for selective binding with the receptor.

The patient sample used in the test will be a biological fluid where the antibodies would normally be found. Blood serum or plasma will usually be employed, while other fluids such as spinal fluid, urine, gastric juice, whole blood, and so on could be used depending upon the particular reagents and antibody involved.

In one of its broadest aspects, the invention involves a reagent kit containing immobilized receptor and labeled ligand used in a process comprising admixing a patient's biological fluid with immobilized receptor, followed by addition of labeled ligand. The relative amount of labeled ligand binding with the immobilized receptor is determined in order to evaluate the qualitative or quantitative presence of the particular auto blocking antibodies in question.

The ligand can be labeled in any known way, such as with a radioactive label, enzyme label, fluorescent label, etc.

Preferably, at least a negative calibrator which is known not to contain any of the particular auto blocking antibody in question is inclined in the reagent kit. More preferably, both a negative calibrator and a positive calibrator are included and processed along with the patient sample. The positive calibrator is a reagent containing an amount of the auto blocking antibody predetermined to just begin to give a positive response in accordance with the sensitivity of the test. This means that any sample falling to the "positive" side of the positive calibrator is "positive" for the presence of the auto blocking antibody and any sample falling between the "negative" and "positive" calibrators would be in a "gray" (that is, indeterminate) area—possibly positive or negative in view of the test sensitivity. Where desired, a strongly positive control can also be run to illustrate a strong positive result and as a double check on the other reagents. In addition, depending upon the type of label used on the ligand, a background control should also be carried out, particularly with a radioactive ligand.

EXAMPLE

A reagent kit having the following six (6) components is used in a radioassay for IF blocking site antibody.

A. Intrinsic Factor (Immobilized receptor protein)

Intrinsic factor (purified hog intrinsic factor) covalently bound to glass particles, which are suspended in 60 ml of 0.03 M phosphate buffered saline (0.15 M) pH 7.4 containing 0.2% sodium azide as a preservative.

B. [$^{57}$Co] Vitamin $B_{12}$ (radio ligand)

[$^{57}$Co] Vitamin $B_{12}$ is dissolved in 120 ml of 0.1 M borate buffer pH 9.3 containing 0.001% potassium cyanide, amaranth red dye (2 $\mu$g/ml) as a pipetting aid, and 0.2% sodium azide as a preservative.

C. Dithiothreitol (optional ingredient to improve non-specific binding)

One vial containing 1.0 ml of dithiothreitol at a concentration optimized for the assay.

D. Negative Calibrator

Consists of stripped defibrinated human plasma. This material can be lyophilized and reconstituted prior to use.

E. Positive Calibrator

A diluted human plasma which contains blocking antibody to intrinsic factor at a concentration determined to be the cutoff point between antibody negatives and antibody positives. The plasma diluent is stripped defibrinated human plasma which does not contain blocking antibodies to intrinsic factor. This material can be lyophilized and reconstituted prior to use. The cutoff point was determined by evaluating approximately 800 normal samples without antibody and approximately 100 samples with blocking antibody. The cutoff point is defined as the response at 3 standard deviations from the mean of normal samples. The positive samples shall not fall within those limits.

F. Positive Control

The positive control is made up of the same materials as the positive calibrator except that an increased amount of blocking antibody is added to give it a strong positive response in the assay.

The various techniques used for storage, reconstitution and handling of the above reagents are known to the skilled artisan. The reagents will be at room temperature when used.

Assay Procedure

It is recommended that the machine background, 100 $\mu$l of negative calibrator and 100 $\mu$l positive calibrator be run in quadruplicate with 100 $\mu$l of other samples being run in duplicate. The average value for each type of sample is used in a calculation as discussed below.

Bearing in mind the above recommendations, the technician will set up the test as follows:

| Tube Number | Contents of Tube |
| --- | --- |
| 1-4 | Empty (for background noise) |
| 5-8 | Negative Calibrator |
| 9-12 | Positive Calibrator |
| 13-14 | Positive Control |
| 15-16 | Serum Sample of Patient |

In other words, at the start of the assay, tubes 5-8 each contain 100 $\mu$l of reagent D, tubes 9-12 each contain 100 $\mu$l reagent E, tubes 13-14 each contain 100 $\mu$l reagent F and tubes 15-16 each contain 100 $\mu$l of the biological fluid sample.

Thereafter a known quantity (0.5 ml) of the immobilized intrinsic factor (reagent A) is added to tubes 5 through 16. The tubes are subjected to agitation and then allowed to incubate at a temperature at which complexation between the intrinsic factor and the antibody can take place, say at room temperature for about two (2) hours. Thereafter, the tubes are centrifuged and decanted. Any endogenous vitamin $B_{12}$ binding protein in the serum sample will be decanted off at this step. A known quantity (1.0 ml) of the radio ligand (reagent B) is added to tubes 5-16, followed by another incubation period, say about one (1) hour at room temperature. Centrifugation is again carried out followed by decantation. The radioactivity of each tube is measured.

If the patient is being administered vitmain $B_{12}$, the patient sample could be treated during the assay to remove any free vitamin $B_{12}$ present, such as, for example by previous admixture of vitamin $B_{12}$ binder to reagent A. Alternatively, vitamin $B_{12}$ binder could be added to tubes 15-16 prior to the addition of the immobilized intrinsic factor. In general, serum samples with as high as 2,000 pg/ml of vitamin $B_{12}$ will not contain enough free vitamin $B_{12}$ to interfere with the assay.

Where used, the dithiothreitol will be added to the samples at the time of addition of the radio ligand as a component of the radioactive vitamin $B_{12}$ solution. The use of this ingredient is optional to improve non-specific binding.

Sample Calculations

All values used are average values reduced by the average background tube count. Since this application of the test is a qualitative one, the calculations involved are simple. One simply divides the net count per minute value from the negative calibrator by the net count per minute value from the positive calibrator to obtain a value (A) which is greater than 1.00. The average net counts from each unknown are then divided into the negative calibrator to obtain a number for each unknown. This number is compared to value (A). From experience, (A) must be greater than or equal to 1.15 for the assay to be considered valid. If the value of an unknown is less than or equal to (A) the unknown is presumptively antibody negative; if the value of the unknown is greater than (A), the unknown is antibody positive. Of course, there is a "gray" (indeterminate) area between (A) and 1.00.

Variations of the invention will be apparent to the skilled artisan. Obviously, the parameters of the incubation periods can vary quite widely, optional washing steps could be employed where desired, separation need not be carried out by centrifugation and decantation, calculations could be carried out in a different manner, values obtained for ligand which does not become bound to the immobilized substrate could be used in calculating a positive or negative response, and so on.

We claim:

1. A process for detecting the presence of intrinsic factor blocking site antibody which comprises:
    (a) admixing a biological fluid sample suspected of containing the blocking antibody with receptor having selective binding sites for said antibody, said receptor being intrinsic factor immobilized on an inanimate support;
    (b) incubating the mixture from step (a) under conditions sufficient to enable substantially all of the blocking antibody present to bind to the receptor, whereby a solid phase comprising said inanimate support with the blocking antibody bound thereto and a liquid phase comprising said biological fluid sample without said blocking antibody result;

(c) separating the solid phase from the liquid phase;

(d) admixing a liquid comprising a labeled ligand for said selective binding sites with the separated solid phase, said ligand being vitamin $B_{12}$;

(e) incubating the mixture from step (d) under conditions sufficient to enable the labeled ligand to bind to the selective binding sites of said receptor which did not bind to said blocking antibody, whereby a second solid phase comprising said inanimate support with at least one of blocking antibody and labeled ligand bound thereto and a second liquid phase comprising unbound labeled ligand result;

(f) separating the second solid phase from the second liquid phase; and (g) determining the amount of labeled ligand present in at least one of the second solid phase and the second liquid phase.

2. The process of claim 1 wherein a known negative calibrator and a known positive calibrator are run as controls.

3. The process of claim 2 wherein the negative calibrator is prepared from human plasma and the positive calibrator is prepared from human plasma containing said suspected blocking antibody.

4. The process of claims 1 or 2 wherein the support is glass particles.

5. The process of claim 4 wherein the receptor is covalently bound to the glass.

6. The process of claims 1 or 2 wherein the label is radioactive, fluorescent, or enzymatic.

7. The process of claim 6 wherein the label is radioactive.

* * * * *